United States Patent
Kalkbrenner et al.

(10) Patent No.: US 8,970,688 B2
(45) Date of Patent: *Mar. 3, 2015

(54) METHOD AND MICROSCOPE FOR THREE-DIMENSIONAL RESOLUTION-ENHANCED MICROSCOPY

(75) Inventors: Thomas Kalkbrenner, Jena (DE); Ralf Wolleschensky, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 410 days.

This patent is subject to a terminal disclaimer.

(21) Appl. No.: 13/499,203

(22) PCT Filed: Aug. 26, 2010

(86) PCT No.: PCT/EP2010/005247
§ 371 (c)(1),
(2), (4) Date: May 24, 2012

(87) PCT Pub. No.: WO2011/038810
PCT Pub. Date: Apr. 7, 2011

(65) Prior Publication Data
US 2012/0224034 A1   Sep. 6, 2012

(30) Foreign Application Priority Data

Sep. 30, 2009 (DE) .......................... 10 2009 043 744

(51) Int. Cl.
*H04N 7/18* (2006.01)
*G02B 21/16* (2006.01)
(Continued)

(52) U.S. Cl.
CPC ............ *G02B 21/16* (2013.01); *G01N 21/6458* (2013.01); *G02B 21/361* (2013.01); *G02B 21/367* (2013.01); *G02B 27/58* (2013.01)
USPC ............. 348/79; 348/49; 422/82.08; 436/172

(58) Field of Classification Search
CPC ........ G02B 1/367; G02B 27/58; G02B 21/16; G02B 21/0076; G02B 21/008; G02B 21/06; G02B 21/00; G02B 21/0036; G02B 21/0072; G02B 21/365; G01N 21/6458; G01N 21/6428; G01N 21/6447
USPC .................... 250/458.1; 348/49, 79; 359/383; 422/82.08; 436/172
See application file for complete search history.

(56) References Cited

U.S. PATENT DOCUMENTS 6,002,459 A    12/1999  Kaise et al.
7,782,457 B2 *  8/2010  Betzig et al. ................... 356/317
(Continued)

FOREIGN PATENT DOCUMENTS

EP     1 083 757 A2   3/2001
JP    2009-105717 A   5/2009
(Continued)

OTHER PUBLICATIONS

Mlodzianoski, MJ,et al;"Experimental characterization of 3D localization techniques for particle-tracking and super-resolution microscopy";Optics Express2009;17(10):8264-8277.
(Continued)

*Primary Examiner* — Sath V Perungavoor
*Assistant Examiner* — Nathnael Aynalem
(74) *Attorney, Agent, or Firm* — Duane Morris LLP

(57) ABSTRACT

The invention relates to a high resolution microscope for three-dimensionally determining the position of objects, in particular individual fluorophores, and preferably for the high spatial resolution luminescence microscopy of a sample, which is marked with marker molecules that can be activated or switched using a signal such that they can be induced to emit certain luminescent radiation only in the activated state. The object is represented by means of an imaging system, preferably the microscope lens, on a surface detector consisting of individual detector elements. At least one microlens array is located in front of the detector elements, and different, preferably adjacent, detector elements receive light from microlenses having different focal lengths and from different object planes, or wherein by means of at least once microlens array, located in part in front of the detector elements, a different object plane is represented on the detector elements in the direction of the light behind the microlenses than on detector elements having no microlenses in front of the latter.

15 Claims, 7 Drawing Sheets

(51) Int. Cl.
*G01N 21/64* (2006.01)
*G02B 21/36* (2006.01)
*G02B 27/58* (2006.01)

(56) References Cited

U.S. PATENT DOCUMENTS

| | | | |
|---|---|---|---|
| 8,217,992 B2 * | 7/2012 | Bewersdorf et al. | 348/47 |
| 2004/0027566 A1 | 2/2004 | Suzuki et al. | |
| 2008/0158666 A1 | 7/2008 | Seale et al. | |
| 2009/0059360 A1 | 3/2009 | Evans et al. | |
| 2009/0237501 A1 | 9/2009 | Lemmer et al. | |
| 2009/0242798 A1 | 10/2009 | Bewersdorf et al. | |
| 2009/0242801 A1 | 10/2009 | Engelhardt et al. | |

FOREIGN PATENT DOCUMENTS

| | | |
|---|---|---|
| KR | 10 2001 0026 891 A | 4/2001 |
| WO | WO 2006/127692 A2 | 11/2006 |

OTHER PUBLICATIONS

Toprak, Erdal, et al.; "Three-Dimensional Particle Tracking via Bifocal Imaging"; Nano Letters 2007; 7(7):2043-2045.

* cited by examiner

■ → Image object plane 1 OE1
▨ → Image object plane 1 OE2

▨ Image object plane 1 OE1
▨ Image object plane 1 OE2
▨ Image object plane 1 OE3 z-localization  x/y-localization in focus   above   below

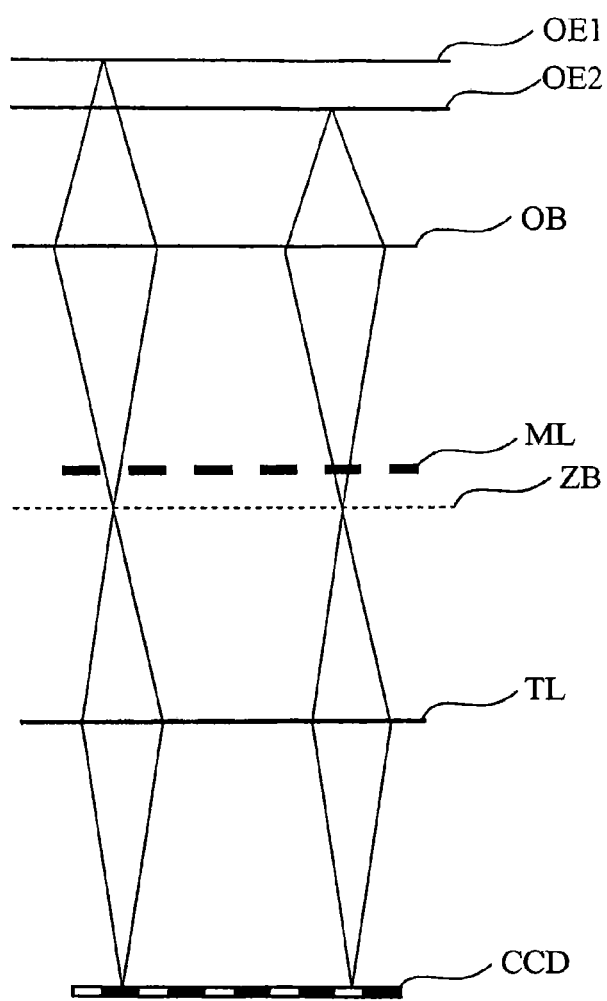

METHOD AND MICROSCOPE FOR THREE-DIMENSIONAL RESOLUTION-ENHANCED MICROSCOPY

RELATED APPLICATIONS

The present application is a U.S. National Stage application of International PCT Application No. PCT/EP2010/005247 filed on Aug. 26, 2010 which claims priority benefit of German Application No. DE 10 2009 043 744.4 filed on Sep. 30, 2009, the contents of each are incorporated by reference in their entirety.

FIELD OF THE INVENTION

The invention relates in particular to a microscope for the spatially high-resolution luminescence microscopy of a sample labeled with marker molecules which can be activated by means of a signal in such a way that they can be excited to emit certain luminescent radiation only in the activated state, wherein the method includes the following steps:
 a) introduction of a signal onto the sample in such a way that only a subquantity of the marker molecules present in the sample are activated, wherein the sample contains subquantities in which the distance between the closest neighboring activated marker molecules is at least greater than or equal to a length resulting from a predefined optical resolution;
 b) excitation of the activated molecules to emit luminescent radiation;
 c) detection of the luminescent radiation with the predefined optical resolution; and
 d) generation of an individual picture from the luminescent radiation captured in step c), wherein the geometrical locations of the marker molecules emitting luminescent radiation are identified by means of a spatial resolution increased above the predetermined optical resolution;
wherein the steps are repeated several times and the plurality of individual pictures obtained in this fashion are combined into a complete image.

BACKGROUND OF THE INVENTION

Luminescent microscopy is a traditional field of application of light microscopy used to analyze biological preparations. In the process, certain dyes (so-called phosphors or fluorophores) are used for the specific labeling of samples, e.g. of cell parts. As mentioned, a sample is illuminated by means of illumination radiation representing excitation radiation and the luminescent radiation induced in this way is recorded with suitable detectors. For this purpose, a dichroic beam splitter combined with block filters are normally provided in the microscope which split the luminescent radiation from the excitation radiation and allow an independent observation. This approach makes it possible to depict individual, differently stained cell parts under the microscope. Of course, a plurality of parts of a single preparation can also be stained simultaneously with different dyes which specifically adhere to different structures of the preparation. This method is referred to as multiple luminescence. Furthermore, it is also possible to measure samples which are luminescent per se, i.e. without the addition of dyes.

As is the rule, luminescence here is the generic term for phosphorescence and fluorescence, meaning that it includes both processes. Whenever the term fluorescence is mentioned in this document, it is deemed a part or aspect of something taken as representative of the whole rather than a limitation.

Laser scanning microscopes (in short LSM) are another known device used for analyzing samples. Of a three-dimensionally illuminated image, they only depict the plane located within the focal plane of the lens by means of a confocal detection array (referred to as a confocal LSM) or a non-linear sample interaction (so-called multiphoton microscopy). An optical cross section is obtained and the documentation of a plurality of optical cross sections in different depths of the sample subsequently makes it possible to generate a three-dimensional image of the sample by means of a suitable data processing device which is composed of the different optical cross sections. Consequently, laser scanning microscopy is suitable for analyzing thick preparations.

Of course, a combination of luminescence microscopy and laser scanning microscopy is also possible, in which a luminescent sample is depicted at different depth planes by means of an LSM.

In principle, the optical resolution of a light microscope, including the one of an LSM is diffraction-limited as a result of the laws of physics. Special illumination configurations for the optimal resolution within these limits are known, such as for example the 4Pi arrangement or arrangements with standing-wave fields. This helps considerably improve the resolution, in particular in an axial direction compared to a traditional LSM. The resolution can be further increased to a factor of up to 10 compared to a diffraction-limited confocal LSM by means of non-linear depopulation processes. Such a method is disclosed for example in U.S. Pat. No. 5,866,911. Different approaches are known for the depopulation processes, such as described for example in DE 4416558 C2, U.S. Pat. No. 6,633,432 or DE 10325460 A1.

A further method for the resolution enhancement is discussed in EP 11579297 B1. In it, non-linear 2
 processes are to be used by means of structured illumination. The published document mentions the fluorescence saturation as non-linearity. The described method claims to realize a displacement of the object space spectrum relative to the transmission function of the optical system by way of structured illumination. Specifically, the displacement of the spectrum means that object space frequencies V0 are transmitted at a spatial frequency of V0-Vm, where Vm is the frequency of the structured illumination. At a given spatial frequency maximally transmissible by the system, this enables the transfer of spatial frequencies of the object exceeding the maximum frequency of the transmission function by the displacement frequency Vm. This approach requires a reconstruction algorithm for the image generation and the utilization of several images for one picture. Furthermore, it is considered a disadvantage of this method that the sample is unnecessarily exposed to radiation outside the detected focus, because the required structured illumination covers the entire sample volume. Moreover, this method can currently not be used for thick samples, because extra-focally excited fluorescence also reaches the detector as background signal and hence drastically reduces the dynamic range of the detected radiation.

A method that achieves a resolution beyond the diffraction limit independently of laser scanning microscopy is disclosed in WO 2006127692 and DE 102006021317. This method abbreviated with the acronym PALM (Photo Activated Light Microscopy) uses a marker substance which can be activated by means of an optical activation signal. The marker substance can only be excited to emit certain fluorescent radiation by means of induction radiation in the activated state. Non-activated molecules of the marker substance will not emit any or at least no noticeable fluorescent radiation even after irradiation with excitation radiation. This means that the activation radiation switches the marker substance into a state in which it can be excited to emit fluorescence. Other types of activation, e.g. of thermal nature, are possible as well. Therefore, this is generally referred to as a switching signal. In the PALM method, the switching signal is applied in such a way that at least a certain ratio of activated marker molecules are spaced apart from adjacent activated molecules such that they are separated as measured by the optical resolution of the microscopy or can be separated retroactively. In other words, the activated molecules are at least for the most part isolated. After exposure to luminescent radiation, the center of their limited resolution-related radiation distribution is determined for said isolated molecules and this determination is used to calculate the position of the molecules with greater accuracy than the optical representation actually allows. Said enhanced resolution by way of mathematically calculated determination of the center of the diffraction distribution is referred to as "superresolution" in the English technical literature. It requires that at least some of the activated marker molecules in a sample are distinguishable, i.e. isolated with the optical resolution used to detect the luminescent radiation. If this is the case, the location information can then be achieved with increased resolution for these molecules.

To isolate individual marker molecules, the PALM method is based on the fact that the probability with which a marker molecule is activated after receiving the switching signal with a given intensity, e.g. a photon of the activation radiation, is identical for all molecules. In other words, the intensity of the switching signal and hence the number of photons striking a unit of area of the sample can be used to make sure that the probability of activating marker molecules present in a given area of the sample is so low that there are enough areas in which only distinguishable marker molecules emit fluorescent radiation within the optical resolution. The result of an appropriate selection of the intensity, e.g. the photon density of the switching signal, is that as much as possible only marker molecules are activated which are isolated relative to the optical resolution and subsequently emit fluorescent radiation. Next, the center of the diffraction-related intensity distribution and hence the position of the marker molecule is mathematically calculated with increased resolution for these isolated molecules. To image the entire sample, the isolation of the marker molecules of the subquantity by way of introducing activation radiation, subsequent excitation and fluorescent radiation imaging is repeated for as long as until as many marker molecules as possible were contained in one subquantity and isolated within the resolution of the image at once.

In the process, the advantage of the PALM method is that no high local resolution is required either for the activation or for the excitation. Instead, both the activation and the excitation can be achieved with wide-field illumination.

As a result, the marker molecules are statistically activated in subquantities by means of suitable selection of the intensity of the activation radiation. For this reason, a plurality of individual pictures need to be evaluated for the generation of a complete image of a sample in which the positions of all marker molecules can be calculated mathematically, e.g. by means of a resolution beyond the diffraction limit. This can concern up to 10,000 individual pictures. As a result, large data quantities are processed and the measurement takes a commensurate amount of time. The acquisition of a complete image alone takes several minutes which is essentially defined by the read-out rate of the camera used. The position of the molecules in the individual pictures is determined by means of complex mathematical procedures such as they are for instance described in Egner et al., Biophysical Journal, p. 3285-3290, volume 93, November 2007. The processing of all individual pictures and the composition into one complete high-resolution image, i.e. an image in which the locations of the marker molecules are illustrated with a resolution beyond the diffraction limit, typically takes one to two hours.

DESCRIPTION OF THE PROBLEM

Prior Art

Literature

[1] Betzig et al., Science 313, 1642-1645 (2006)
[2] Hess et al., PNAS 104, 17370-17375 (2007)
[3] Hess et al., Biophys J. 91, 4258-427 (2006)
[4] Shroff et al., PNAS 104, 20308-2031 (2007)
[5] Rust et al., Nat Methods 3, 793-796 (2006)
[6] Egner et al., Biophys J. 93, 3285-3290 (2007)
[7] Toprak et al., Nano Lett. 7, 3285-3290 (2007)
[8] Juette et al., Nature Methods 5, 527 (2008)
[9] Huang et al., Science 319, 810 (2008)
[10] Holst/Lomheim, CMOS/CCD sensors and camera systems, SPIE Press (2007)
[11] Lessard et al., Appl. Phys. Lett. 91 224106 (2007)

The basic methods as described above have also been described extensively in the literature in a number of variations [1-6].

The variants (PALM, STORM, D-STORM etc.) mainly differ in the selection of the fluorophores and the type of optical switching process.

However, all methods have the localization of the molecules by way of reproduction on a high-sensitivity (e.g. EMCCD) camera in common.

In the process, the quasi point-shaped light source (molecule) to be detected is imaged onto a plurality of camera pixels by means of the point spread function (PSF) of the microscope.

The exact position of the molecule in the x/y plane can now be determined either by means of fitting the known PSF (Gaussian) function or by determining the center of gravity or by means of a mixture of both (Gaussian mask).

The typical localization accuracies range between 5 and 30 nm (depending on the experimental conditions); this also corresponds to approximately the achievable lateral resolution of this method.

In practice, the requirement that the molecules are not positioned too densely next to each other on the one hand and that the reproduction of analyzed structures is as complete as possible on the other hand means that many individual pictures (typically 20,000) of a sample need to be taken.

The positions of the molecules active at the time are determined and archived in each picture. This means that the already considerable time required to take 20,000 pictures is further extended by the (depending on the algorithm and computer system used) even significantly longer time required for the calculation or evaluation, before the actual high-resolution image is available.

However, the method of localization-based high resolution described above is restricted to surfaces or 2 dimensions, respectively, because the localization of the individual dye molecules in the third spatial direction (z-direction) is far more complex.

Several approaches have been described in the literature in this context, which are briefly explained below.

Astigmatism/Cylindrical Lens ([9]):

With this approach, a weak cylindrical lens is introduced into the detection light path, which results in an astigmatic PSF. Analogously, the picture of the molecule is elliptically distorted if the molecule is located above or below the point of symmetry of the PSF. The information about the z-position of the molecule can then be extracted from the orientation and scope of the distortion.

One problem of this method is that the local environment and the orientation of the molecular dipole can also result in a distortion of the spot of the molecule.

Depending on their orientation, an incorrect z-value would in this case be assigned to these molecules.

Detection in Two Planes: Bewersdorf et al., Toprak et al. ([7, 8]):

A 50/50 beam splitter is introduced into the detection light path which splits (duplicates) the picture into two partial pictures. These two pictures are either imaged onto two identical cameras or side-by-side onto a camera chip. An optical path length difference is introduced into one of the two partial light paths in such a way that two object planes result from the two partial light paths, with a distance from each other of about one half or one z-PSF (700 nm) in the z-direction. The z-position for molecules positioned between these two planes can now be determined, e.g. by subtracting the two partial pictures of the molecule or by fitting a three-dimensional PSF.

Two high-sensitivity cameras are required for this method or both pictures need to be arranged side-by-side onto a camera chip. The latter naturally results in a restriction of the picture field. Furthermore, both variants require a precise adjustment of the light paths or calibration measurements to ensure the overlapping of the two partial pictures with sub-pixel accuracy. Alternatively, the pictures need to be superimposed by means of a computer (software).

Solution:

The solutions according to the invention are the subject of the independent patent claims.

Preferred updates are described in the subclaims.

BRIEF DESCRIPTION OF THE DRAWINGS

The invention is explained in more detail below, for example based on the attached drawings which also disclose essential invention-related characteristics. In the figures:

FIG. 10 shows a representation of microlenses in or close to the intermediate image plane.

EMBODIMENTS OF THE INVENTION

Figure 1:
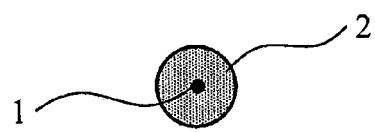
FIG. 1 shows a schematic representation of an activated marker molecule in a resolution-limited volume.

FIG. 1 shows a schematic representation of a marker molecule 1 which was excited to emit fluorescence. Of course, the detection of fluorescence requires a plurality of excitations, because every excitation delivers exactly one fluorescence photon and the detection of radiation requires the integration of many fluorescence photons. Due to the principles of physics, the fluorescent radiation emitted by the marker molecule 1 can only be detected with a limited optical resolution in a microscope. Even if the microscope achieves the diffraction limit of optical resolution, the photons of the fluorescent marker molecule 1 are still scattered because of the diffraction and hence detected in an Airy disk 2. In other words, instead of the geometrical extension of the marker molecule 1 which is schematically drawn as a black circle in FIG. 1, the microscope strictly reproduces a larger object, represented by the Airy disk 2 in FIG. 1. The size of the Airy disk 2 depends on the quality of the microscopic device used and is defined by the half width of the point-spread function of the optical image formation. In effect, this does not concern a two-dimensional object, but a diffraction volume in which the fluorescence photons end up. However, the latter appears as a disk in the two-dimensional representation of FIG. 1. The term "Airy disk" is therefore used generally to describe a maximum resolution volume which can be achieved by the lens system used. However, the lens system used must not necessarily operate at the diffraction limit, even though this is preferable.

In order to be able to localize the marker molecule 1 more accurately within the Airy disk 2, the PALM method already described in general above is used. It activates individual marker molecules, wherein in this description the term activation generally refers to the activation of certain luminescence properties of the marker molecules, i.e. both the activation of the luminescence excitability as well as a change of the luminescent emission spectrum, which corresponds to the activation of certain luminescent properties. In the exemplary embodiment described here, the activation is achieved with optical activation radiation. However, other, non-optical activation mechanisms are possible as well.

The activation is carried out such that there are at least several activated molecules whose center of gravity is not in the Airy disk of other activated molecules, i.e. which are at least still distinguishable within the optical resolution.

Figure 2:
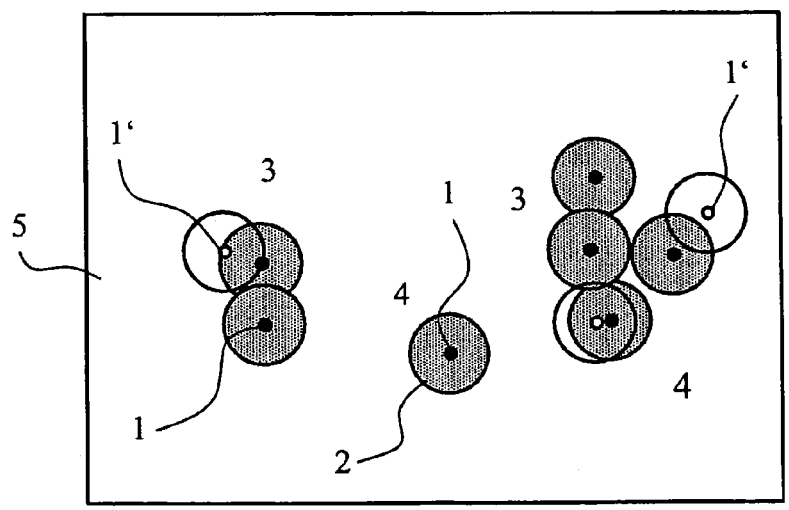
FIG. 2 shows a schematic representation of the imaging of different activated and non-activated marker molecules onto a spatially resolving detector.

FIG. 2 shows a schematic representation of an exemplary situation on a detector 5, which integrates the photons with location resolution. As can be seen, there are areas 3 in which the Airy disks of neighboring marker molecules overlap. As seen in the left-hand area 3 of FIG. 2, only the marker molecules which were activated beforehand are relevant in this context. Non-activated marker molecules 1' do not emit the certain fluorescent radiation collected on the matrix detector 5, and hence do not play a role.

In the areas 4, e.g. the area 4 located in the middle of the matrix detector 5, marker molecules 1 are positioned in such a way that their Airy disk 2 does not overlap with an Airy disk of another activated marker molecule 1. The right-hand area of the matrix detector 5 shows that areas 3 in which Airy disks of activated marker molecules overlap can definitely be adjacent to areas 4 in which this is not the case. Furthermore, the right-hand area 4 demonstrates that the proximity of an activated marker molecule 1 to a non-activated marker molecule 1' does not play a role for the detection, because such a marker molecule 1' does not emit the fluorescent radiation detected by the matrix detector 5, and hence is not fluorescent.

Figure 3:
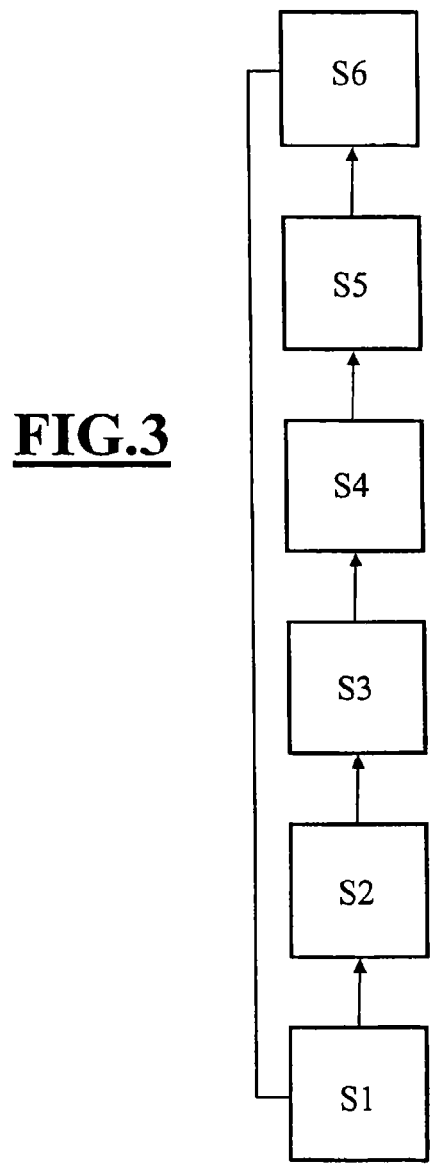
FIG. 3 shows a flow chart for the image generation in the PALM method.
Figure 4A:
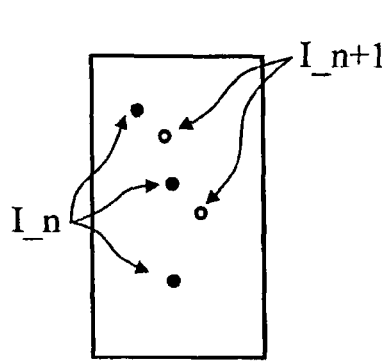
FIG. 4 shows explanatory representations relating to the flow chart of FIG. 3 of marker molecules imaged onto the detector of FIG. 2.
Figure 4B:
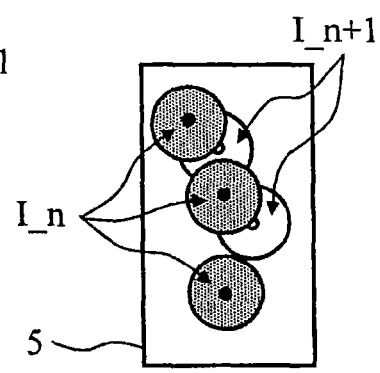
Figure 4C:
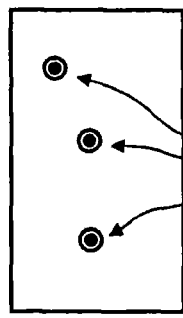
Figure 4D:
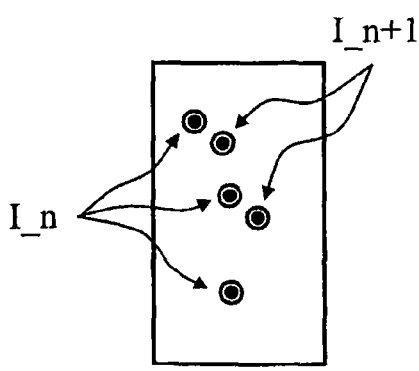

In order to capture a picture beyond the optical resolution determined by the device, said image being a high-resolution image within the meaning of this description, the steps schematically illustrated in FIG. 3 are now used.

In a first step S1, a subquantity of the marker molecules are activated by means of a switching signal; in other words, they are switched from a first state in which they cannot be excited to emit the certain fluorescent radiation to a second state in which they can be excited to emit the certain fluorescent radiation. Of course, the activation signal can also induce a selective deactivation, i.e. an inverse procedure can also be used in step S1. What matters is that after step S1 only a subquantity of the marker molecules can be excited to emit the certain fluorescent radiation. The activation or deactivation (for simplicity's sake, only the case of activation is described hereinafter), takes place irrespective of the used marker molecules. With a dye such as e.g. DRONPA, PA-GFP or reversibly switchable synthetic dyes (such as Alexa/Cyan constructs), the activation is achieved with optical radiation and hence the switching signal is switching radiation.

The partial picture a in FIG. 4 shown under FIG. 3 shows the state after step S1. Only a subquantity of the marker molecules I_n is activated. The marker molecules of this subquantity are represented with a solid black spot. The remaining marker molecules have not been activated in this step. They are labeled I_n+1 in the partial picture a of FIG. 4.

Marker molecules which have been activated can then be excited to emit fluorescent radiation in a second step S2. Fluorescent proteins known from the prior art such as PA-GFP or DRONPA are preferably used as fluorescent dyes. These molecules are activated with radiation in the range of 405 nm, the fluorescent radiation is excited at a wavelength of about 488 nm, and the fluorescent radiation lies within a range above 490 nm.

The emitted fluorescent radiation is detected in a third step S3, for example by integrating the absorbed fluorescent photons, so that the situations illustrated in the partial picture b at the bottom of FIG. 4 occur on the matrix detector 5. As can be seen, the Airy disks of the activated marker molecules I_n do not overlap. The size of the Airy disks is defined by the optical resolution of the reproduction onto the matrix detector 5. Additional (theoretical) Airy disks of fluorescent molecules are shown in the partial picture b of FIG. 4, which are not part of the non-activated group I_n+1. Because said non-activated marker molecules do not emit fluorescent radiation, no fluorescent radiation contained in their (theoretical) Airy disks interferes with the detection of the fluorescent radiation of the subquantity I_n of the activated marker molecules.

To ensure that as few Airy disks as possible overlap in the subquantity I_n such that the marker molecules are no longer distinguishable, the activation energy is adjusted such that the subquantity I_n accounts for only a relatively small proportion of the total quantity of marker molecules, so that statistically many marker molecules are distinguishable relative to the volume resolvable with the optical arrangement.

In a fourth step S4, the position of the fluorescent marker molecules is mathematically calculated from the diffraction distribution of the fluorescence disks, whereby the resolution with which the position of the activated marker molecules is known is sharpened beyond the resolution of the optical arrangement, as illustrated in partial picture c of FIG. 4.

Alternatively to a computational determination, it is generally possible to amplify the recorded fluorescent radiation non-linearly and hence to sharpen the resolution beyond the optical arrangement in an economical way. The non-linear amplification can for example be described according to the function $S=A \cdot F^N$ (equation 1) or $S=A \cdot \exp^{F/W}$ (with $w=10^{-N}$ (equation 2)), wherein F is the amplitude of the fluorescent signal, A is a scaling factor and N an integer greater than 1. A strong non-linear dependence of parameter S from F is particularly advantageous, i.e., for example high values for N in the equations 1 or 2. Of course, other functions can be used as well. Basically, the non-linearity is selected such that the half width of the Airy disk corresponds to a desired spatial resolution of the position indicator of the marker molecules. In addition to non-linear amplification, it is also possible to use non-linear attenuation. With it, fluorescent signals of low amplitude or intensity are attenuated, whereas strong signals remain at least largely unattenuated. Of course, a combination of non-linear amplification and attenuation can also be used.

In a fifth step S5, the marker molecules whose position information is precisely known are now combined into an individual picture whose spatial resolution is increased beyond the optical resolution. However, it only contains information about the previously activated subquantity of marker molecules.

In a sixth step S6, the individual picture is integrated into a complete image in a known manner. Next, the method returns to step S1, wherein the previously fluorescent molecules need to be deactivated again. Depending on the type of marker molecule, the deactivation can be achieved by separate radiation or by subsidence of the activation state. Furthermore, it is also possible to bleach previously imaged marker molecules with excitation radiation.

An additional individual picture which contributes to the complete image is obtained with every cycle. A different subquantity of marker molecules is activated in the next cycle, e.g. the subquantity I_n+1 illustrated in FIG. 4.

The repetition of steps S1 to S6 is used to compile the complete image with individual pictures of the individual cycles, which indicate the locations of the marker molecules with a spatial resolution which is sharpened compared to the resolution of the optical image formation. As a result, a high-resolution complete image is successively compiled with a corresponding number of iterations. In the process, the Airy disk is preferably reduced in all three spatial dimensions in the method, when a plurality of image stacks spaced apart in the z-direction are recorded. This way the complete image contains the high-resolution spatial information of the marker molecules in all three spatial directions.

Figure 5:
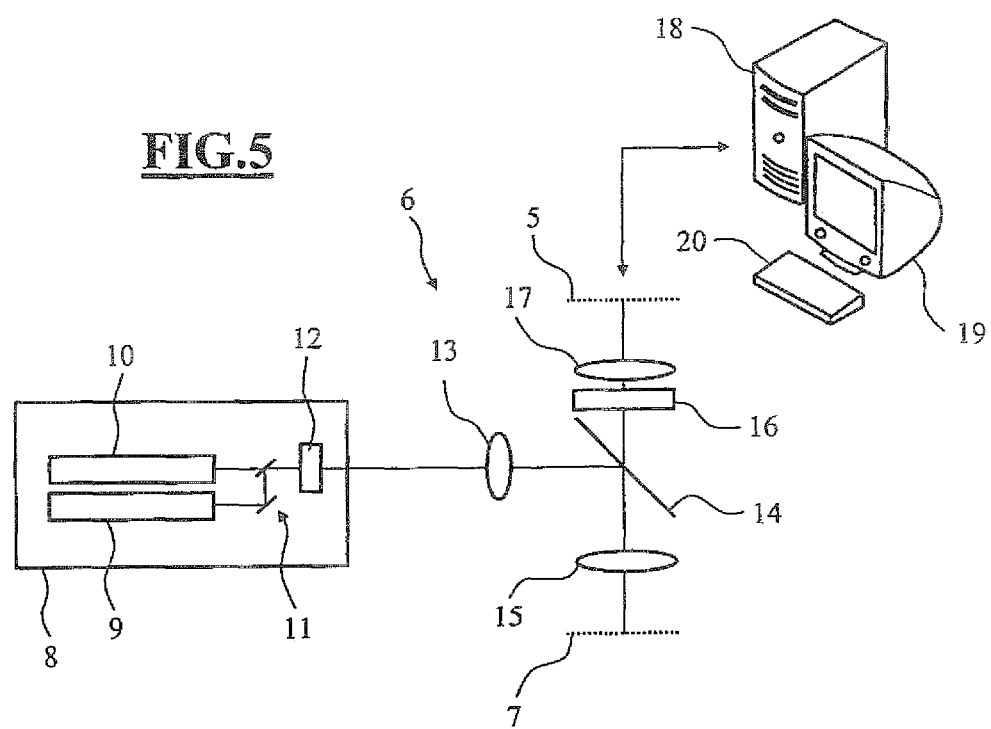
FIG. 5 shows a schematic representation of the microscope for PAL microscopy.

FIG. 5 shows a schematic representation of a microscope 6 for the high-resolution imaging of a sample 7. The sample is labeled for example with the dye DRONPA (cp. WO 2007009812 A1). For activation and fluorescence excitation purposes, the microscope 6 comprises a radiation source 8 which has individual lasers 9 and 10, whose beams are combined with a beam merger 11. The lasers 9 and 10 can emit radiation for example at 405 nm (activation radiation) and 488 nm (fluorescence excitation and deactivation). Further dyes are known (e.g. the dye named DENDRA (cp. Gurskaya et al., Nature Biotech., volume 24, p. 461-465, 2006)) with which the activation and fluorescence excitation can take place at the same wavelength. In this case, one laser will suffice.

An acousto-optic filter 12 is used for selecting the wavelength and for the quick switching or attenuation of individual laser wavelengths. A lens system 13 focuses the radiation into a pupil of an object lens 15 via dichroic beam splitter 14 so that the radiation of the radiation source 8 falls onto the sample 7 as wide-field illumination.

Fluorescent radiation accumulating in the sample 7 is collected via the object lens 15. The dichroic beam splitter 14 is designed in such a way that it allows the fluorescent radiation to pass so that it reaches a tube lens 17 through a filter 16 and as a result, the fluorescent sample 7 is imaged onto the detector 5 as a whole.

A control device is provided to control the operation of the microscope 6, which is designed here as computer 18 with display 19 and keyboard 20. The methodical steps S2 to S6 are performed with the computer 18. In the process, the image rate of the matrix detector is relevant for the total measuring time and therefore a matrix detector 5 with an image rate as high as possible is advantageous to reduce the measuring time.

The core ideas of the present invention are explained in more detail below:

1. Camera Sensor Having at Least 2 Integrated Object Planes:

The main idea in this case is the generation of at least 2 object planes separated in the vertical (z) direction with the use of only one camera and without changing the microscopic beam path. This is not achieved by splitting the image and introducing an optical path length difference between the partial images as in [8], but by nesting two subimages into each other on a camera sensor (FIG. 1 on the right-hand side). In principle, this could be achieved by arranging the nested pixels at different heights on the sensor. However, this is difficult to realize, because the necessary splitting of two object planes into z of ~700 nm with a typically used 100× object lens would require a pixel level difference of ~700 nm*^(100)^2=7 mm.

Aside from production-related difficulties, a typical lateral pixel size of just 8-16 μm would result in an extremely unfavorable relationship. Without microlenses, a pixel on the same sensor would have to be elevated by 7 millimeters compared to its neighboring pixel, with a pixel size of only 8-16 micrometers. Even if the manufacture were possible, only the pixels on the top would actually "see" a picture.

Instead, the z-offset of the two object planes can be achieved with a microlens (ML) array on the sensor (FIG. 1 on the left-hand side) or alternatively in the imaging beam path.

The use of ML arrays on CCD or CMOS sensors to increase the filling factor is a common procedure (e.g. [10] and references contained therein).

With the arrangements proposed here, the z-offset can be adjusted advantageously with the selection of the focal length of the MLs. The MLs are not assigned to every pixel, but alternatingly, so that the exposure generates two subimages which correspond to two object planes separated in the z-direction.

The idea is not only limited to the pixel arrangement illustrated in FIG. 1.

In a further embodiment, 3 object planes can be integrated for example with the use of two different microlens groups. Depending on the data evaluation, this results in 3 support locations for the data adjustment in the z-direction and hence potentially greater accuracy. A possible packing-dense arrangement with three assigned object planes on the basis of the hexagonal super-CCD structure (Fuji) is outlined in FIG. 7.

FIG. 6 illustrates the creation of two object planes separated in the z-direction through microlens arrays.

Figure 6A:
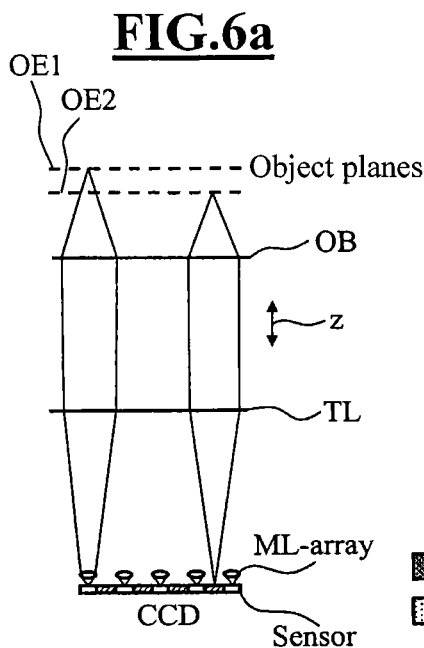
FIG. 6 shows an embodiment of the invention with a microlens array.

FIG. 6a) contains a schematic representation of the sensor plane CCD, wherein microlenses ML are each arranged (two-dimensionally) alternating with gaps before the individual sensor elements in an array.

Object planes OE1 and OE2 are imaged onto a sensor CCD via the object lens OB and a tube lens TL.

Because of the ML array used for the depiction of the object plane OE1, the object planes OE1 and OE2 are not arranged on a single plane, but are offset to each other in the z-direction. In the illustration on the right-hand side, the observer sees different z-planes corresponding to different focal lengths, here characterized with the colors black and gray.

Figure 6B:
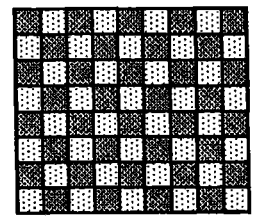

In FIG. 6b), the sensor pixels assigned to object plane OE2 are illustrated with lighter shades of gray, while the sensor pixels assigned to object plane OE1 are illustrated with darker shades of gray.

Here, they are arranged symmetrically by way of symmetrical arrangement of the ML array. However, deviations from said symmetry are also possible within the scope of this invention.

Advantages of this approach include in particular that only one camera and one beam path are required.

The alignment of two subimages relative to each other is automatically achieved, with a constant and known 1-pixel offset.

Any microscope or any other optical system would be directly advantageously upgradable to this kind of 3D high-resolution system, without modification of the beam path and without additional optical components.

Figure 7:
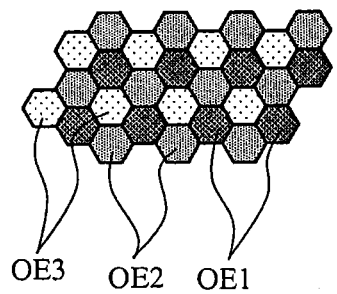
FIG. 7 shows a distribution of detection elements.

FIG. 7 shows a possible pixel and ML array for the creation of three object planes separated in the z-direction through a microlens array with two different focal lengths.

The image planes OE2 and OE3 are created with ML arrays having different focal lengths. Similar to FIG. 1, OE1 is an object plane arranged on a detector element without a microlens.

However, three ML arrays each with a different focal length can also be provided.

Contributions from other object planes are only perceived as diffuse background for the individual pixels.

The object lens used (see PALM method and cited literature) has a very short focal length (high NA), meaning that objects outside the focal length are detected very blurry (diffuse).

The elements can be confocal (corresponding to an Airy unit), but they are generally larger in size or the imaging is performed in this fashion.

2.) ML Array as in 1), but in the Intermediate Image, such as Illustrated e.g. in FIG. 10:

An additional optical element (the ML array) indeed needs to be introduced into the beam path (into an intermediate image ZB), but the advantages (only one camera and beam path, automatic alignment, upgradability) are preserved.

However, the ML array could advantageously be configured and manufactured separately, without depending on the camera chip manufacturer in this respect. Conveniently, the intermediate image would be designed enlarged, so that the tolerances of the ML array are relaxed.

In the process, the microlenses could be positioned slightly in front of the ZB plane (or behind as illustrated with negative focal length), so that their focal plane is within the ZB or the sensor position is adjusted accordingly.

If a plurality of ML arrays are used with e.g. 2 different focal lengths as illustrated above, the intermediate image can advantageously be positioned between the two focal planes of the ML arrays.

On the detected spot, a spot positioned precisely in the intermediate image plane appears equally out of focus for both detected receiver arrays which are assigned to the respective ZL arrays.

Advantageously, differences with respect to the detected blurriness would allow a precise detection of the position of the particle by means of the detected blurriness within the detected depth range without z-adjustment of the array (for example 700 nm).

3.) At Least 2 Object Planes with Adjusted "Superpixels" with Substructure:

This kind of substructure can be used advantageously for 2 or 3 object planes such as for example in FIG. 7 as well as FIGS. 5 and 6.

Figure 8A:
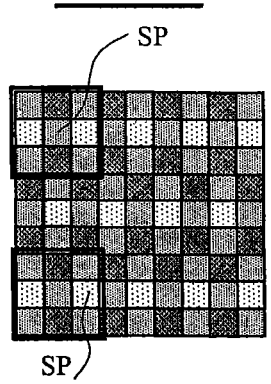
FIG. 8 shows combined "superpixels" for the three-dimensional evaluation.

Suitable superpixels can be defined in particular for CMOS cameras with random access pixels, which allow the direct allocation of the position information of each superpixel. This approach would be advantageous for real-time localization per superpixel in 3D and hence e.g. for tracking individual objects by way of moving the sample and adjusting it to an individual superpixel tracking signal. In essence a PSD (Position Sensitive Detector) per superpixel is realized. Especially the superpixel arrangement in FIGS. 8*a, b* and *c* on the right-hand side would be suitable for particle tracking as described in [11].

In contrast to [11], a wide-field detection method (camera) could be linked directly with 3D particle tracking without any additional optical elements. This approach is in particular not restricted only to high-resolution microscopy with high-sensitivity cameras, but it can also be realized with economical cameras for correspondingly fast specimens. One example includes e.g. the tracking of beads or vesicles with many fluorophores, or even the realization of optical tweezers integrated in the wide-field microscope.

With CMOS cameras for instance, every pixel can be addressed individually.

As illustrated, several pixels (for example 9) are looked at as one "superpixel" and allocated jointly to one evaluation unit (storage unit) by way of evaluation—see black frame on the picture.

Such a superpixel would for example detect an image spot.

A plurality of these kinds of superpixels would be arranged side-by-side on the sensor.

Their size can be adjusted to the expected size of the spots (molecules) to be analyzed, for example with corresponding optical imaging or by adjusting the size on the receiver.

Information about the lateral and axial position of the image spot (molecule) can be obtained from its substructure by means of addition and subtraction.

Figure 8B:
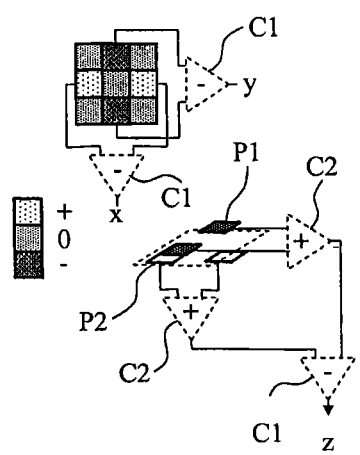
Figure 8C:

Specifically, FIG. 8 illustrates a) possible "superpixels" (black rectangles) SP, consisting of a plurality of individual pixels with object planes as coded in the legend (+, 0, −), corresponding to different shades of gray.

In turn, the individual object planes can be realized by means of ML arrays on the camera chip and/or in the intermediate picture planes as described under 6) and 7).

In FIG. 8*b, d*, logic levels used to deduct—C1 (x, Y-direction) or add—C2 (+) the signals of for example two pixels that contain signals from the same object plane and then subtract the added signals from each other (Z-direction) are in each case connected to the pixels which correspond to different object planes.

As in FIG. 7, the different shades of gray represent contributions from different object planes. For example, in 8*c* if a molecule M denoted with a dotted line moves to the left, the detected values of the symmetrically arranged detector elements of the superpixel (e.g. the light gray on the right and left side of the center pixel Pz) are not equal. By means of subtraction and with the corresponding sign, the direction of the movement, i.e. the amount of the movement, can be calculated using the absolute value of the inequality.

This can be done with both the horizontally arranged pixels (X) as well as the vertically arranged pixels (y) in the drawing in order to obtain complete two-dimensional information about the movement.

In the Z-direction, the intensity of the upper and lower focal plane of the ML for example with 3 different focal planes, represented with different sensor elements, is analogously compared by means of the shades of gray as illustrated, and the movement or the position of the analyzed spot within the recorded depth range is also recorded in this manner by comparing the recorded intensity.

8*d*) illustrates the respective plus/minus +/− link of pixels P1, P2 which capture different object planes and the subsequent subtraction to obtain the Z-information with respect to their amount and their sign.

A possible other connection of the detector elements of a superpixel is illustrated in 8*c* on the right-hand side, which is only partly symmetrical or has a different axis of symmetry. The remarks concerning the determination of the position and movement above apply analogously here.

Every pixel/superpixel of the presented arrangements can be used as a position-sensitive detector like described above (comparable to a quadrant photodiode). This way, a pair of optical tweezers can be realized with the presented camera and the high-resolution microscope alone. The fundamentals for optical tweezers can be found e.g. in: http://en.wikipedia.org/wiki/Optical_tweezers or in the references cited therein. If combined with an LSM, the actual tweezers, i.e. the focused holding laser, can be realized by means of a laser integrated in the LSM. Said focused spot, which forms the actual optical trap, can be positioned as desired by means of the LSM scanner. The fast scanning and switching function (AOTF) also allows the creation and positioning of a plurality of spots.

Once a particle (vesicle, bead, depending on the experiment) has been 'trapped,' the superpixel at the location of its depiction can be 'added on' as a PSD. If the particle is now exposed to forces and it is easily deflected from its resting position, it is possible to detect this movement.

With respect to the tracking procedure: in connection with a 3D piezo test plate, it is also possible to track diffusion and transport processes of individual objects with one of the superpixels: the superpixel at the image location of the particle is again 'added on' and the position signal is kept at "zero" in all directions (x, y, z) via a feedback loop. The piezo control voltage required for this purpose is directly proportional to the position change of the tracked particle.

Advantages include in particular:

Combined LSM/fluorescence microscopy/high-resolution microscopy/particle tracking/optical tweezers in a single system. All of these methods are of interest in the field of molecular cell biology but currently require separate dedicated systems.

As a result, this approach is also economical, because only one of the expensive components (laser, camera) is required.

Figure 9:
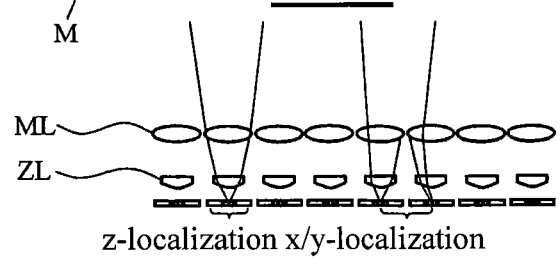
FIG. 9 shows a combination of microlens and cylindrical lens array.
Figure 9:
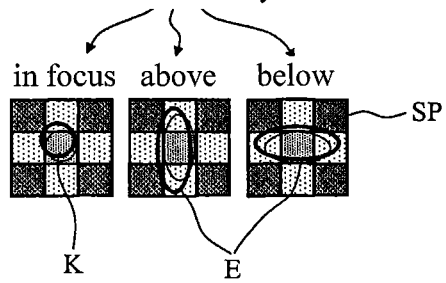

4. Combination of Microlenses and Cylinder Lenses to Acquire X/Y/Z-Information:

FIG. 9 illustrates the z-localization by combining a microlens array ML and a micro cylinder lens array ZL together with a suitable superpixel structure. As is known from the PALM method, the x-y localization can be obtained from the intensity information of the central pixel or the sum of signals of all nine pixels of every superpixel.

However, the z-information here is acquired in a similar fashion to [9]—see section about the prior art—by integrating an astigmatic focus. However, in addition to the microlens array ML as described above, a cylinder microlens array ZL is additionally integrated in such a way that the symmetrical result, the x/y-localization for objects (molecules) in the focus can only be performed with the central pixels without signal loss. A sagittal or meridional ellipsoid E results for a spot source located above or below the object plane assigned to said circle of confusion.

The advantage of the arrangement is that the z-information of the observed spot source can be gathered directly from the marginal pixel signals of every superpixel. Especially the state-of-the art CMOS camera chip architecture which enables the direct control and read-out of pixels (random access) would allow a direct allocation of the intensity and hence the z-information of every superpixel without software fit. The x-y-localization can be acquired as known from the PALM method based on the intensity information of the central pixel or the sum of the signals of all nine pixels of every superpixel.

The combination of cylinder lens and microlenses essentially represents an anamorphotic lens system integrated into the convergent beam path after the tube lens.

In front of the focal plane of the arrangement, the focusing effect of the microlens ML and the effect of the cylinder lens ZJ which is restricted to one axis cooperate and create a spot-shaped focus K (picture on the left-hand side, small circle) in the focal plane and an ellipsoid E in front of the focal plane (picture in the middle, black ellipse) and after the focal plane (picture on the right-hand side, black ellipse), said ellipsoid comprising a different (sagittal and meridional) orientation for a spot source located above or below the object plane.

With the occurrence of the ellipsoid, a signal is detected in the elements adjacent to a central detector element, wherein the orientation of the ellipsoid (detection by means of horizontal or vertical neighboring elements in the example, such as also described in FIG. 8) and the detector elements (vertical or horizontal) thus generating a signal characterize whether the object is located above or below the object plane.

In contrast to the invention, in the printed document 9, the recorded image is evaluated by means of a pixel-by-pixel read-out of the image and software-assisted determination of the luting.

Disadvantages include in particular

Transfer and evaluation of large data quantities (basic problem with Palm). The solution presented here offers the possibility of realizing the position assignment already on the camera (in an FPGA) and transferring only the evaluated data.

The applications described under 3) including tweezers and/or tracking are not possible with this 'traditional' approach.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for high-resolution microscopy for three-dimensional determination of the position of objects, in particular individual fluorophores, for spatial high-resolution luminescence microscopy of a sample labeled with marker molecules which can be activated or switched by means of a signal in such a way that they can be excited to emit certain luminescent radiation only in the activated state, wherein the method comprises the following steps:

a) introduction of a signal onto the sample in such a way that only a subquantity of the marker molecules present in the sample are activated, wherein the sample contains subquantities in which the distance between the closest neighboring activated marker molecules is at least greater than or equal to a length resulting from a predefined optical resolution, b) excitation of the activated molecules to emit luminescent radiation, c) detection of the luminescent radiation with the predefined optical resolution, and d) generation of an individual picture from the luminescent radiation captured in step c), wherein the geometrical locations of the marker molecules emitting luminescent radiation are identified by means of a spatial resolution increased above the predetermined optical resolution, wherein the steps are repeated several times and the plurality of individual pictures obtained in this fashion are combined into a complete image, and wherein an object is imaged onto a surface detector consisting of individual detector elements by means of an imaging system, preferably the microscope lens, wherein a different object plane is imaged onto the detector element in the direction of light behind the microlenses than onto the detector element in front of which no microlenses are located through at least one microlens array which is partly located in front of the detector elements.

2. The high-resolution microscopy method according to claim 1, further comprising symmetrical distribution of the microlenses.

3. The high-resolution microscopy method according to claim 1, wherein a different object plane is imaged onto detector elements in the direction of light behind the microlenses than onto the detector elements in front of which no microlenses are located.

4. The high-resolution microscopy method according to claim 1, wherein the microlenses are arranged in front of the detector and/or in or in the vicinity of an intermediate image plane.

5. A method of high-resolution microscopy for three-dimensional determination of the position of objects, in particular individual fluorophores, for spatial high-resolution luminescent microscopy of a sample labeled with marker molecules which can be activated or switched by means of a signal in such a way that they can only be excited to emit certain luminescent radiation in the activated state, wherein the method comprises the following steps:

a) introduction of the signal onto the sample in such a way that only a subquantity of the marker molecules present in the sample are activated, wherein the sample contains subquantities in which the distance between the closest neighboring activated marker molecules is at least greater than or equal to a length resulting from a predefined optical resolution, b) excitation of the activated molecules to emit luminescent radiation, c) detection of the luminescent radiation with the predefined optical resolution and d) generation of an individual picture from the luminescent radiation captured in step c), wherein the geometrical locations of the marker molecules emitting luminescent radiation are identified by means of a spatial resolution increased above the predetermined optical resolution, wherein the steps are repeated several times and the plurality of individual pictures obtained in this fashion are combined into a complete image, and wherein an object is imaged onto a surface detector consisting of individual detector elements by means of an imaging system, preferably the microscope lens, wherein at least one microlens array is located in front of the detector elements and different, preferably neighboring detector elements obtain light from microlenses with different focal lengths and from different object planes.

6. The high-resolution microscopy method according to claim 5, wherein the microlenses are arranged in front of the detector and/or in or in the vicinity of an intermediate image plane.

7. A method for high-resolution microscopy for three-dimensional determination of the position of objects, in particular individual fluorophores, for the spatial high-resolution luminescent microscopy of a sample labeled with marker molecules which can be activated or switched by means of a signal in such a way that they can be excited to emit certain luminescent radiation only in the activated state, wherein the method comprises the following steps:
  a) introduction of the signal onto the sample in such a way that only a subquantity of the marker molecules present in the sample are activated, wherein the sample contains subquantities in which the distance between the closest neighboring activated marker molecules is at least greater than or equal to a length resulting from a predefined optical resolution,
  b) excitation of the activated molecules to emit luminescent radiation,
  c) detection of the luminescent radiation with the predefined optical resolution and
  d) generation of an individual picture from the luminescent radiation captured in step c), wherein the geometrical locations of the marker molecules emitting luminescent radiation are identified by means of a spatial resolution increased above the predetermined optical resolution, wherein the steps are repeated several times and the plurality of individual pictures obtained in this fashion are combined into a complete image, and wherein
  an object is imaged onto a surface detector consisting of individual detector elements by means of an imaging system, preferably the microscope lens, and one or a plurality of detector elements arranged around a central detector element are jointly evaluated in such a way that a two- or three-dimensional position recognition and/or object recognition is achieved by mathematically linking the signals of the detectors arranged around a central detector element and by compiling location- and/or movement-related information based on the mathematical result and/or its sign.

8. A microscope for carrying out the method of claim 7, wherein detectors are arranged in a horizontal plane (X, Y) and/or a vertical plane (X,Z; Y,Z).

9. The microscope according to claim 7, wherein the imaging onto at least one detector element is performed by means of an anamorphotic imaging element for the determination of a Z-position of an object.

10. The microscope according to claim 9, where the spatial location in Z is determined based on the distortion of the detected image.

11. The microscope according to claim 9, wherein the anamorphotic element is a combination of microlenses and cylinder lenses.

12. The microscopic method, according to claim 1 for the generation of a three-dimensionally resolved image, further comprising imaging objects onto a surface detector consisting of individual detector elements by means of an imaging system, and where a different object plane is imaged onto the detector elements in the direction of the light behind the microlenses than onto detector elements in front of which no microlenses or microlenses with a different focal width are located through at least one microlens array which is located at least partly in front of the detector elements.

13. The microscopic method, according to claim 1, wherein one or a plurality of detector elements of a surface detector arranged around a central detector element are jointly evaluated in such a way that a two- or three-dimensional position recognition and/or object recognition is achieved by mathematically linking the signals of the detectors arranged around a central detector element and by compiling the location and/or movement information based on the mathematical result and/or its sign.

14. The method according to claim 1 further comprising tracking one or a plurality of particle pathways.

15. The method according to claim 1 wherein said method is used in a pair of or as optical tweezers.

* * * * *